United States Patent
Ekberg

[11] Patent Number: 6,162,193
[45] Date of Patent: Dec. 19, 2000

[54] ULTRASOUND PROBE

[75] Inventor: Lars Ekberg, Vattholma, Sweden

[73] Assignee: Forskarpatent I Uppsala AB, Uppsala, Sweden

[21] Appl. No.: 08/945,398

[22] PCT Filed: Mar. 15, 1996

[86] PCT No.: PCT/SE96/00334

§ 371 Date: Sep. 15, 1997

§ 102(e) Date: Sep. 15, 1997

[87] PCT Pub. No.: WO96/28213

PCT Pub. Date: Sep. 19, 1996

[30] Foreign Application Priority Data

Mar. 16, 1995 [SE] Sweden .................................. 9500930

[51] Int. Cl.[7] ............................ A61B 17/20; A61B 17/22
[52] U.S. Cl. ............................................. 604/22; 606/127
[58] Field of Search ................................ 604/22, 27, 28,
604/35; 600/459, 452, 466; 606/128, 127, 107

[56] References Cited

U.S. PATENT DOCUMENTS

| | | |
|---|---|---|
| 3,528,410 | 9/1970 | Banko . |
| 3,857,387 | 12/1974 | Shock . |
| 3,942,519 | 3/1976 | Shock . |
| 4,531,934 | 7/1985 | Kossovsky et al. ........................ 604/22 |
| 4,579,123 | 4/1986 | Chen et al. ............................. 128/660 |
| 4,679,558 | 7/1987 | Kensey et al. ........................... 606/128 |
| 4,901,709 | 2/1990 | Rattner ................................... 606/128 |
| 4,908,015 | 3/1990 | Anis ........................................ 606/166 |
| 4,928,672 | 5/1990 | Grasser et al. ........................... 606/128 |
| 4,928,697 | 5/1990 | Hsu . | |
| 4,945,913 | 8/1990 | Krasnicki et al. . |
| 5,042,984 | 8/1991 | Kensey et al ............................ 606/159 |
| 5,156,143 | 10/1992 | Bocquet et al. ........................... 604/22 |
| 5,191,560 | 3/1993 | Lobentanzer et al. .................... 606/128 |
| 5,879,356 | 3/1999 | Geuder .................................... 606/107 |

FOREIGN PATENT DOCUMENTS

| | | |
|---|---|---|
| 945417 | 7/1949 | Germany . |
| 1120784 | 12/1961 | Germany . |
| 4011017 | 10/1991 | Germany . |
| 4034533 | 1/1992 | Germany . |
| 4122590 | 1/1992 | Germany . |
| 4136004 | 1/1993 | Germany . |
| 9112046 | 8/1991 | WIPO . |
| 9320783 | 10/1993 | WIPO . |

*Primary Examiner*—Sharon Kennedy
*Attorney, Agent, or Firm*—Young & Thompson

[57] ABSTRACT

A body (40) is provided which is inserted between an ultrasound crystal (30) and an output port (27) in a probe filled with a fluid, to centrally defocus generated ultrasound and create an output ultrasound field having limited propagation, especially for higher intensities, after passing the output port. The casing is divided into three portions (21, 22, 23), whereby a front conical portion (21) including the output port (27) and the centrally defocusing body (40) is easily replaceable. The fluid in the casing is refilled via a tube connection (12) to a fluid storage connected as a communicating vessel to the ultrasound device. Moreover, the output port of the device is provided with a thin membrane (10), preferably of replaceable latex rubber, which is attached to prevent the fluid in the casing from emerging, but at the same time enabling the effective transfer of generated ultrasound. The membrane (10) may be attached by placing an O-ring gasket in a circularly formed slot (25) on the conical portion.

11 Claims, 1 Drawing Sheet

ULTRASOUND PROBE

TECHNICAL FIELD

The present invention relates to an ultrasound probe, and particularly to a defocusing device for an ultrasound generator forming and delimiting an outgoing ultrasound field, for instance in the field of medical applications.

PRIOR ART

In connection with the treatment of glaucoma, there is a general desire to treat this disease without necessarily resorting to direct surgical operation on the eye. It is known that in a glaucoma condition, small particles are gradually clogging the filter, which forms the so called trabecular meshwork, thereby increasing the pressure in the eye caused by the continuing building up of the eye aqueous fluid, that can not be drained in a natural manner, thus causing harmful pressure to the eye. Apart from the usual treatment by means of using various kinds of eye drops, there are a number of patent documents describing different instruments for the treatment of glaucoma, to mention among others WO 91/12046 and WO 93/20783, which are related to transplantation of a drainage device into the eye, to in an artificial manner control the pressure in the eye. A number of documents, for example U.S. Pat. Nos. 4,928,697 and 4,945,913 describe devices used to measure the pressure in the eye without making direct contact to the eye itself. Furthermore there are other devices described which comprise ultrasound probes which are surgically applied into the eye to remove unwanted tissue. Examples of such devices are: U.S. Pat. No. 3,528,410, U.S. Pat. No. 3,857,387 and U.S. Pat. No. 3,942,519.

A new method, which recently has been proposed, is based upon by means of ultrasound having a specially designed field form generated, so to say, to from outside the eye shake out the particles clogging the drainage path of the eye aqueous fluid. In order to achieve this, an ultrasound probe is required being able to produce a suitable ultrasound field, which may be concentrated just around the trabecular meshwork such that during the treatment it will not affect or damage other parts of the sensitive eye.

There are known many different forms of ultrasound generators. Examples of such generators appear for instance in the German patent documents: DE 945 417, DE-1 120 784, DE-4 011 017, DE-4 034 533, DE-4 122 590 and DE-4 136 004. The first one of these generators (DE 945 417) was disclosed already in 1956, while the last one (DE-4 136 004) dates back to 1991. DE 945 417 discloses an absorption cover, preferably of felted material which can attenuate production of standing waves. DE-1 120 784 discloses a membrane consisting, for example, of an electromechanical active ceramic material, like barium titanate, for transmission of ultrasound waves from the generator to a medium.

DE-4 011 017 discloses a device for generating focused shock waves provided with two-sided shock wave sources, whereby the sources are of different types and focusing takes place by moving the sources in relation to each other.

From the last three mentioned patent documents (DE-4 011 017, DE-4 122 590 and DE-4 136 004) DE-4 034 533 discloses a shock wave source with focusing of the generated pressure pulses to a convex lens serving as a focusing zone, whereby the upper face of the convex lens forming the output sound surface presents a form different from the necessary form for focusing of the pressure pulses.

DE-4 122 590 additionally discloses a shock wave generator having a focusing means, whereby at the same time there are means, the defocusing action of which is adjustable and less than the action of the focusing means. The disclosed design is primarily intended for splitting up renal stones whereby its purpose is to create a considerably larger focusing zone in order to manage splitting up large stones. This design is not applicable for the treatment of the eye according to the suggested method.

Finally DE-4 136 004 discloses a generator for generation of acoustic waves with a liquid lens adjusting the focal distance and thereby moving the focal point of the acoustic waves. The design moreover discloses a complicated construction which is not applicable for the purpose of treating eyes according to the suggested method.

DESCRIPTION OF THE INVENTION

According to the present invention, an ultrasound device is disclosed, which can generate an adapted ultrasound field, applicable, for example, in an suggested method for treatment of glaucoma, which device can be directed towards the trabecular meshwork of an eye without affecting or harming the other parts of the sensitive eye in such a treatment.

According to a first objective of the present invention, a body is inserted between the ultrasound crystal and an output port of the fluid filled portion of the device in order to centrally defocus the generated ultrasound and provide a reduced ultrasound field having a limited propagation of primarily higher intensities after passing the output port.

According to a second objective of the present invention, the casing is divided into several portions, whereby a forward conical front portion, including the output port and the centrally defocusing body, is easily replaceable, whereby fluid in the probe is refilled via a tube joint connected to a liquid storage acting as a communicating vessel to the probe.

According to a third objective of the present invention, the output port is provided with a thin replaceable membrane, preferably of latex rubber, fixedly held by an fixing means to prevent the fluid from emerging, but at the same time enabling effective transfer of the generated ultrasound, whereby the fixing means consists of an O-ring gasket placed in a circular slot of the conical portion.

Further objectives and purposes of the present invention are set forth below.

BRIEF DESCRIPTION OF THE DRAWINGS

The invention will be described in form of a preferred illustrative embodiment by means of the attached drawings, wherein same reference numbers indicate equal or corresponding members, and where.

DESCRIPTION OF AN ILLUSTRATIVE EMBODIMENT

Figure 1:
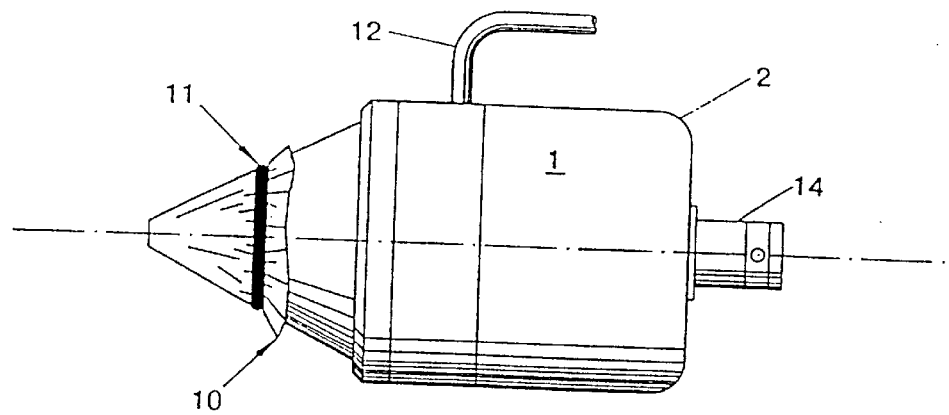
FIG. 1 demonstrates an illustrative embodiment of an ultrasound probe according to the present invention.

FIG. 1 presents an illustrative embodiment of an ultrasound probe according to the present invention. The probe, totally designated as 1, presents a casing 2 consisting of three portions, according to FIG. 2, a front conical portion 21, a central portion 22 provided with a tube connection 12, and a rear portion 23 provided with a coaxial socket 14, preferably of type BNC. The front conical portion 21 additionally, in its outer conical surface, is provided with a circular slot 25 in order to receive an O-ring gasket 11. The O-ring gasket is used to secure in position a membrane 10, preferably a portion of a condom, to flexibly close a front opening port 27 of the front conical portion 21.

Between the central portion 22, which is threaded into the rear portion 23, an ultrasound crystal 30 is inserted, the center of which will then abut a spring biased electrically conducting plate 31 through a spring 32 electrically connected to the center pin of the BNC socket 14.

The tube connection 12 onto the central portion 22 is connected by a suitable flexible tube to a fluid storage (not shown), preferably containing distilled water.

Thus the portions 21 and 22 of the assembled device, are filled with fluid acting as transmission medium for the ultrasound waves, which are electrically generated by means of the crystal 30. The very thin membrane 10 covering the opening 27 prevents the fluid from emerging, but does not prevent the generated ultrasound waves from propagating further through the opening 27 towards an outer medium in contact with the membrane.

The crystal 30, which preferably in the preferred embodiment normally has a thickness of about 0.5 to 0.9 mm abuts the outer edge of the side facing the conical portion 21 and against a slightly inclined flange 33 in the central portion 22, and which is adopted to the crystal 30. The flange 33 is then arranged to make electrical contact with the side of the crystal facing the conical portion and thereby connecting it to the outer sleeve of the BNC socket. The flange 33 also centers the crystal 30 in the device. To electrically make connection, an electrically conductive material is used which at the same time serves as sealing substance to prevent the space behind the crystal 30 from being filled with fluid.

For instance, in a preferred embodiment of the ultrasound probe, preferably a nylon or teflon ring (not shown) is positioned against the circumferential edge of the crystal 30 at the side facing the BNC socket and which ring further is pressed against the crystal 30 by a strong helical spring (not shown) and which has an external diameter corresponding to the internal diameter of the rear portion 23. Rear portion 23 contains a power connection to an active driven electrode of the ultrasound crystal (30). By means of this latter arrangement, the crystal is ensured to maintain its position during operation and that no liquid may leak into the rearmost space area. Moisture eventually leaking will, according to the state of the art, be detected by the electronic unit feeding power to the crystal 30.

Additionally there is, inside the conical portion 21, centered a body 40, preferably made of rubber. In the illustrated embodiment the body 40 has the form of a cone with rounded top, and it is centered with great precision in the conical portion 21 by means of three beams 41. In the illustrative embodiment the beams 41 or thin stable booms are made of thin injection needles which have a small spacing rivet soldered at the ends facing the body 40, the rivet defines exactly how deep the beams should reach into the, in advance designed, fastening holes in the body 40 to guarantee a good centering therein. The other ends of the three beams 41, according to the disclosed embodiment, are attached to the inner wall of the conical portion 21.

Figure 2:
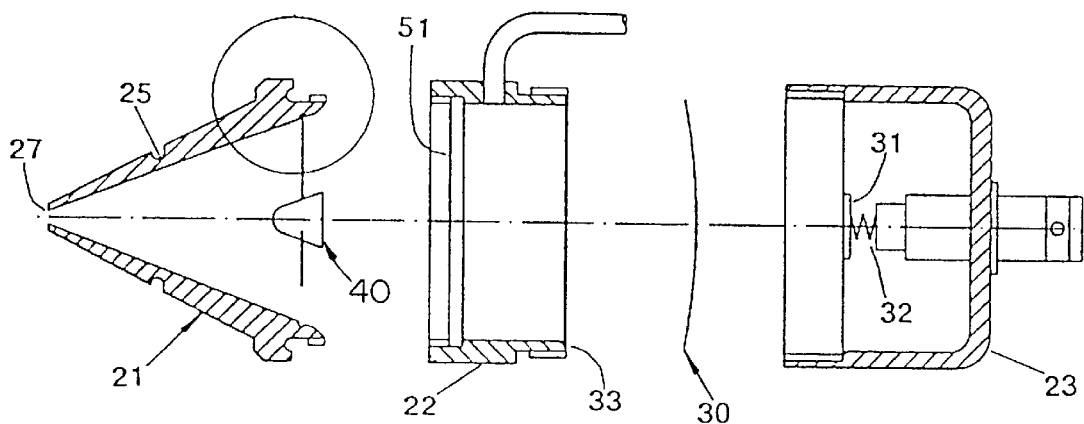
FIG. 2 demonstrates a cross section of a disassembled ultrasound probe according to FIG. 1.
Figure 4:
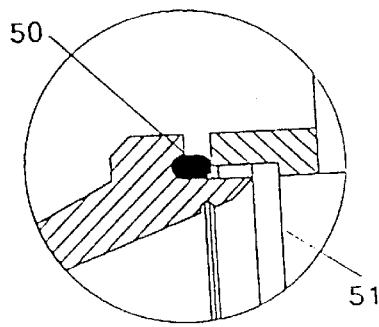
FIG. 4 demonstrates an enlarged cross section view of the adjustment device of the ultrasound probe.
Figure 3:
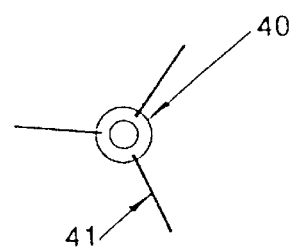
FIG. 3 demonstrates a front view of an illustrative embodiment of a defocusing member according to the present invention.

The conical portion 21 is attached to the central portion 22 by a threaded attachment, whereby an oval O-ring gasket 50, shown enlarged in FIG. 4, seals the connection between the two sections 21 and 22. The O-ring gasket 50 is made oval to allow an exact adjustment of the conical portion, and thereby the body 40, relative to the crystal 30. The oval cross section of the O-ring 50 allows a position range variation of about 1 mm between the portions 21 and 22 with a retained satisfactory sealing quality. In FIG. 2 and 4, 51 designates a clearance zone for the conical portion 21.

The device, according to the illustrated embodiment, may operate with replaceable conical portions 21, which, for example, may have different length and/or different sized output opening, and/or a different body 40. In a preferred embodiment of the present invention the opening 27 of the conical portion 21 is slanted about 10°–15° (not seen in FIG. 2) relative to the longitudinal axis of the conical portion 21 to obtain an easy application of the device to the area middle over the trabecular meshwork of the eye. Even a larger slanting of the opening 27 could be advantageous in a particular operation with the device. Before utilization, the portion 21 will be assembled to the rest of the casing and a fluid connection is made to a storage container, for instance a plastic bag filled with distilled water or saline. Such liquid bags are well known in the technical field. By keeping the device 1 at a suitable height in relation to the liquid bag, fluid will flow into the device 1. The device should preferably be held with its opening 27 directed upward so that when the device is fully filled, the water will be pressed out through the opening 27. By properly balancing the height, as stated above, and utilizing the fluid surface tension, fluid is obtained all the way out to the discharge opening of the portion 21, and thus, all air has been evacuated from the device. At this point, a piece of latex rubber, in the simplest case a piece of a condom, will be placed over the opening 27, and the latex rubber will be tightened over the conical portion by means of rolling upwards a suitable O-ring gasket 11 until it locks into the slot 25.

At this stage, the device is ready for use after, in addition, the tip of the conical portion 21 preferably has been provided with a smear of gel to be able to transmit the ultrasound to an area, middle over the trabecular meshwork of the eye, to be treated.

In a case when the device will be used for the treatment in connection to glaucoma, the tip having the gel is placed carefully to the area middle over the trabecular meshwork and the crystal 30 is powered and thereby an ultrasound field is obtained, the energy of which is intended, only of an order of 0.6 to 1 mm, to be active into the eye, according to the present state of the art. The probe 1 is then moved carefully around the iris along the trabecular meshwork.

Thus the desired effective field pattern of the active ultrasound is obtained through the combination of the shape of the conical portion and the form of the body 40 and its central position in front of the crystal 30 according to the present invention, whereby a direct wave from the crystal is restricted from propagating through the opening 27 and into the eye, where such a wave could reach too deep and even could be harmful. A number of standard portions 21 could be manufactured, based on the medical requirements for field patterns of the ultrasound.

The ultrasound device according to the present invention can of course be modified in various ways by a person skilled in the art without departing from the spirit and scope of the invention as being defined in the attached claims.

What is claimed is:

1. An ultrasound probe (1) for generating an ultrasound field, comprising a casing (2) having a liquid-filled inner space, liquid in said liquid-filled inner space allowing the propagation of an ultrasound field, and an ultrasound crystal (30) mounted in the casing (2), the ultrasound crystal being powered by a source of electricity which is connected to the ultrasound crystal by a socket (14) mounted on the casing (2), the ultrasound crystal delimiting the liquid-filled inner space in one direction and generating the ultrasound field, the casing (2) further comprising an output port (27), and the ultrasound probe further comprising a body (40) arranged in the liquid-filled inner space between the ultrasound crystal (30) and the output port, for centrally defocusing a generated ultrasound field.

2. Ultrasound probe according to claim 1, wherein said body (40) is mounted radially centered with respect to the casing (2) by thin stable booms (41) connected to an inner surface of the casing (2).

3. Ultrasound probe according to claim 1, wherein said body (40) is a conical body of cast rubber, said conical body having a rounded tip.

4. Ultrasound probe according to claim 1, wherein the casing (2) is divided into a number of portions (21, 22, 23), of which a front conical portion (21) includes the output port (27) and is removably couplable to a central portion (22) by threads provided on the front conical portion and the central portion, and wherein the casing (2) comprises a tube connection (12) for refilling the casing (2) with liquid, said tube connection being connectable to a liquid storage means in such a way that the casing and said liquid storage means function as communicating vessels.

5. Ultrasound probe according to claim 4, wherein said output port (27) comprises a replaceable membrane (10) secured onto the front conical portion by a rubber O-ring (11) fitted into a locking groove provided on an outer circumference of said front conical portion (21), whereby said membrane prevents liquid from emerging at said output port yet enables an effective transfer of generated ultrasound.

6. Ultrasound probe according to claim 4, wherein connection between said front conical portion (21) and said central portion (22) of the casing (2) is provided with sealing means (50) for enabling fine adjustment of the distance between said output port (27) and the ultrasound crystal (30), whereby a coupling between said front conical portion and said central portion is achieved by complementary threading of the respective front conical portion and said central portion.

7. Ultrasound probe according to claim 4, wherein said body (40) is mounted radially centered with respect to the casing (2) by thin stable booms (41) connected to an inner surface of said front conical portion (21).

8. Ultrasound probe according to claim 2, wherein the ultrasound crystal (30) abuts against said central portion (22) of the casing (2) in such a way that a liquid-tight seal is achieved, thereby preventing liquid from penetrating into a rear space in a rear portion (23) of the casing (2), and further wherein said rear portion (23) contains a power connection to an active driven electrode of the ultrasound crystal (30).

9. Ultrasound probe according to claim 1, wherein said output port (27) is an opening in said front conical portion, said opening being angled relative to a longitudinal axis of said front conical portion, whereby in use said angle of said opening permits an inclined position of the ultrasound probe.

10. Method for treating a glaucoma condition by using ultrasound, comprising the steps of selecting an ultrasound crystal (30) mounted in a casing (2), powered by a source of electricity connected to the casing;

providing, in the casing (2), an output port (27) for transmitting therethrough ultrasound waves generated by the ultrasound crystal;

providing, in a space between the ultrasound crystal (30) and said output port (27), a liquid for transferring the ultrasound waves generated by the ultrasound crystal (30) to the output port (27);

providing, in the casing, a radially centered body (40) between the ultrasound crystal (30) and the output port (27), for centrally defocusing the ultrasound waves; and arranging, over the output port (27) of the casing (2), a membrane (10) for preventing liquid in the space between the crystal (30) and the output port (27) from emerging from said output port (27), and for transferring the ultrasound waves from the output port (27) to an object brought into contact with said membrane (10).

11. Method according to claim 10, comprising the further steps of applying a suitable gel to the membrane (10);

bringing said membrane (10) with the suitable gel into contact with an area located over the trabecular meshwork of an eye; and energizing the ultrasound crystal (30) for generating a centrally defocused ultrasound field for clearing the aqueous fluid channels of the eye from particles blocking these channels.

* * * * *